(12) United States Patent
Goldenberg et al.

(10) Patent No.: US 7,220,399 B2
(45) Date of Patent: May 22, 2007

(54) ALPHA OR BETA EMITTERS ATTACHED TO FRAGMENTS IN RADIOIMMUNOTHERAPY

(75) Inventors: David M. Goldenberg, Mendham, NJ (US); Thomas M. Behr, Goettingen (DE)

(73) Assignee: Center For Molecular Medicine and Immunology, Belleville, NJ (US)

( * ) Notice: Subject to any disclaimer, the term of this patent is extended or adjusted under 35 U.S.C. 154(b) by 619 days.

(21) Appl. No.: 10/724,397

(22) Filed: Dec. 1, 2003

(65) Prior Publication Data

US 2004/0180001 A1    Sep. 16, 2004

Related U.S. Application Data

(62) Division of application No. 09/588,565, filed on Jun. 7, 2000, now Pat. No. 6,667,024.

(60) Provisional application No. 60/138,635, filed on Jun. 7, 1999.

(51) Int. Cl.
    *A61K 9/14* (2006.01)
    *A61K 9/16* (2006.01)
    *A61K 9/47* (2006.01)

(52) U.S. Cl. ..................... 424/1.49; 424/1.69

(58) Field of Classification Search ............ 424/1.11, 424/1.37, 1.49, 9.3, 9.34, 9.341, 489, 1.69
    See application file for complete search history.

(56) References Cited

U.S. PATENT DOCUMENTS 4,831,122 A * 5/1989 Buchsbaum et al. ..... 530/391.3
5,641,471 A * 6/1997 Geerlings ................ 424/1.49

FOREIGN PATENT DOCUMENTS

| WO | WO 96/29087 | * 9/1996 |
| WO | WO 96/40245 | 12/1996 |
| WO | WO 96/40425 | * 12/1996 |

OTHER PUBLICATIONS

Shaun B. Jones et al., Evaluation of Dithiol Chelating Agents as potential Adjuvants for Anti-IL-2 Receptor Lead or Bismuth Alpha Radioimmunotherapy. Nucl. Med. & Biol, vol. 23, 105-113, 1996.*
Casey, J. L., et al., "Clearance of yttrium-90-labelled anti-tumour antibodies with antibodies raised against the 12N4 DOTA macrocycle" British Journal of Cancer (1998) 78(10), 1307-1312 XP-000986994.
Rowlinson-Busza, Gail, et al., "90Y-Labeled Antibody Uptake by Human Tumor Xenografts and The Effect of Systemic Administration of EDTA" Int. J. Radiation Oncology Biol. Phys., vol. 28, No. 5, pp. 1257-1265 1994.
Denardo, Sally J., et al., "Yttrium-90/Indium-111-DOTA-Peptide-Chimeric L6: Pharmacokinetics, Dosimetry and Initial Results in Patients with Incurable Breast Cancer" Anticancer Research 17: 1735-1744 (1997).

Adams, G. P., et al., "Delivery of the a-Emitting Radioisotope Bismuth-213 to Sold tumors via Single-Chain Fv and Diabody Molecules" Nuclear Medicine & Biology, vol. 27, pp. 339-348, 2000.
Behr, Thomas M., et al., "High-Linear Energy Transfer (LET) a versus Low-LET B Emitters in Radioimmunotherapy of Solid Tumors: Therapeutic Efficacy and Dose-limiting Toxicity of 213Bi-versus 90Y-labeled CO17-1A Fab' Fragments in a Human Colonic Cancer Model" Cancer Research 59, 2635-2643, Jun. 1, 1999.
Govindan, Serengulam V., et al., "90 Yttrium-Labeled Complementarity-Determining-Region-Grafted Monoclonal Antibodies for Radioimmunotherapy: Radiolabeling and Animal Biodistribution Studies" Bioconjugate Chem. 1998, 9, 773-782.
Wong, Jeffrey Y. C., et al., "A Phase I Radioimmunotherapy Trial Evaluating 90 Yttrium-labeled Anti-Carcinoembryonic antigen (CEA) Chimeric T84.66 in Patients with Metastatic CEA-producing Malignancies" Clinical Cancer Research, vol. 6, 3855-3883, Oct. 2000.
Davis, Ila A. et al., "Radioimmunotherapy Using Vascular Targeted 213Bi: The Role of Tumor Necrosis Factor a in the Development of Pulmonary Fibrosis" Clinical Cancer Research 3160s vol. 5, 3160s-3164s, Oct. 1999 (Suppl.).
Watanabe, Naoyuki, et al., "CaNa2 EDTA for Improvement of Radioimmunodetection and Radioimmunotherapy with 111in and 90Y-DTPA-Anti-CEA MAbs in Nude Mice Bearing Human Colorectal Cancer" The Journal of Nuclear Medicine, vol. 41, No. 2, Feb. 2000, pp. 338-344.
Jones, Shaun B. et al. "Evaluation of Dithiol Chelating Agents as Potential Adjuvants for Anti-IL-2 Receptor Lead or Bismuth Alpha Radioimmunotherapy" Nuclear Medicine & Biology, vol. 23, pp. 105-113, 1996.
Goodwin, D. A., et al., "Monosional antibody hapten radiopharmaceutical delivery" Nuclear Medicine Communications 7, 569-580 (1986).
Juweid, Malik E., et al., "Phase I/II Trial of 131I-MN-14 F(ab)2 Anti-Carcinoembryonic Antigen Monoclonal Antibody in the Treatment of Patents with Metastatic Medullary Thyroid Carcinoma" Cancer Apr. 15, 1999, vol. 85, No. 8, p. 1828-1842.
Karacay, et al., "Development of a Streptavidin-Anti-Carcinoembryonic Antigen Antibody, Radiolabeled Biotin Pretergeting Method for Radioimmunotherapy of Colorectal Cancer. Reagent Development" Bioconjugate Chem. 1997, 8, 585-594.

(Continued)

Primary Examiner—Michael G. Hartley
Assistant Examiner—Jagadishwar R. Samala
(74) Attorney, Agent, or Firm—Faegre & Benson LLP

(57) ABSTRACT

The present invention relates to radioimmunoconjugates useful in targeted radioimmunotherapy and methods of treating a patient using radioimmunoconjugates. The radioimmunoconjugates of the present invention comprise an alpha- or beta-emitting radioisotope and a binding site linked to or on an antigen-binding fragment of an antibody which specifically binds to a tumor-associated antigen. The methods of treating a patient can include administering one or more clearing agents to the patient in conjunction with the radioimmunoconjugate of the present invention, as well as subsequently grafting bone-marrow or autologous stem-cells to the patient.

14 Claims, No Drawings

OTHER PUBLICATIONS

Behr, Thomas M., et al., "Phase I/II Clinical Radioimmunotherapy with an Iodine-131-Labeled Anti-Carcinoembryonic antigen Murine Monoclonal Antibody IgG" The Journal of Nuclear Medicine, vol. 38, No. 6, Jun. 1997, pp. 858-870.

Ullen, Anders, et al. "Use of Anticytokeratin Monoclonal Anti-Idiotypic Antibodies to Improve Tumor: Nontumor Ratio in Experimental Radioimmunolocalization" Cancer Research (Suppl.) 55, 5868s-5873s, Dec. 1, 1995.

Ong, Gaik Lin, et al. "The fate of antibodies and their radiolabels bound to tumor cells in vitro: the effect of cross-linking at the cell surface and of anti-idiotype antibodies" Cancer Immunol Immunotherapy (1994) 39: 325-331.

Sharkey, Robert M., et al., "Clinical Evaluation of Tumor Targeting with a High-Affinity, Anticarcinoembryonic-Antigen-Specific, Murine Monoclonal Antibody, MN-14" Cancer Mar. 15, 1993, vol. 71, No. 6 pp. 2082-2846.

Pimm, M. V., et al. "Influence of syngeneic monoclonal anti-idiotypic antibodies to murine Monoclonal antibodies against tumour-associated antigens on the biodistribution of their target antibodies and their fragments" J Cancer Res Clinical Oncology (1993) 119:408-414 pp. 408-414.

Schiele, J., et al., "The effect of unlabeled monoclonal antibody (mAb) on the biodistribution of 131I-anti-idiotype mAb in murine B cell lymphoma" Radiotherapy and Oncology. 24 (1992) 169-176 pp. 169-176.

Sharkey, Robert M., et al., "Enhanced Clearance of Radiolabeled Murine Monoclonal Antibody by a Syngeneic Anti-Idiotype Antibody in Tumor-Bearing Nude Mice" Int. J. Cancer 51, 266-273 (1992).

Goldenberg, David M., et al., "Targeting, Dosimetry, and Radioimmunotherapy of B-Cell Lymphomas with Iodine-131-Labeled LL2 Monoclonal Antibody" Journal of Clinical Oncology, vol. 9, No. 4 (Apr. 1991), pp. 548-564.

Stewart, J. Simon W., et al., "Clearance of 131I-labeled Murine Monoclonal Antibody from Patients' Blood by Intravenous Human Anti-Murine Immunoglobulin Antibody" Cancer Research 50, 563-567, Feb. 1, 1990.

Blumenthal, Rasalyn D. et al., "Reduction by Anti-Antibody Administration of the Radiotxicity Associated with 131I-Labeled Antibody to Carcinoembryonic Antigen in Cancer Radioimmunotherapy" Journal of the National Cancer Institute vol. 81, No. 3, Feb. 1989.

Pimm, M. V., et al., "The Influence of Syngeneic Anti-Idiotypic Antibody on the Blodistribution of an anti-tumour monoclonal Antibody in Balb/c Mice" Int. J. Cancer: 43, 147-151 (1989).

Sharkey, Robert M., et al., "Factors Influencing Anti-Antibody Enhancement of Tumor Targeting with Antibodies in Hamsters with Human Colonic Tumor Xenografts" Cancer Research 48, 2005-2009, Apr. 15, 1988.

Goldenberg, David M., et al., "Anti-Antibody Enhancement of Iodine-131 Anti-CEA Radioimmunodetection in Experimental and Clinical Studies" The Journal of Nuclear Medicine, vol. 28, No. 10, Oct. 1987, pp. 1604-1610.

Sharkey, Robert M., et al. "Clinical Evaluation of Tumor Targeting with a High Affinity, Anticarcinoembryonic-Antigen-Specific, Murine Monoclonal Antibody, MN-14" Cancer Mar. 15, 1993, vol. 71, No. 6, pp. 2082-2096.

Behr, Thomas, et al., "High-Linear Energy Transfer (LET) a versus Low-LET B Emitters in Radioimmunotherapy of Solid Tumors: Therapeutic Efficacy and Dose-limiting Toxicity of 213Bi-versus 90Y-labeled CO17-1A Fab' Fragments in a Human Colonic Cancer Model1" Cancer Research59, 2635-2643, Jun. 1, 1999, XP-000982262.

Govindan, Serengulam V., et al., "90Yttrium-Labeled Complementarity-Determining-Region-Grafted Monoclonal Antibodies for Radioimmunotherapy: Radiolabeling and Animal Biodistribution Studies" Bioconjugate Chem., vol. 9, No. 6, 1998, 773-782 XP-000982306.

Casey, J. L., et al., "Clearence of yttrium-90-labelled anti-tumour antibodies with antibodies raised against the 12N4 DOTA Macrocyle" British Journal of Cancer (1998) 78(10), 1307-1312 XP-000986994.

Rowlinson-Busz, Gail, et al., "90Y-Labeled Antibody Uptake by Human Tumor Xenografts and The Effect of Systemic Administration of EDTA" Int. J. Radiation Oncology Biol. Phys., vol. 28, No. 5, pp. 1257-1265, 1994 XP-000986989.

* cited by examiner

ALPHA OR BETA EMITTERS ATTACHED TO FRAGMENTS IN RADIOIMMUNOTHERAPY

BACKGROUND TO THE INVENTION

1. Field of the Invention

The present invention relates to improved methods of delivering radioisotopes to tumor cells for effecting targeted radioimmunotherapy (RAIT). More specifically, the present invention relates to a radioimmunoconjugate wherein an alpha- or beta-emitting radioisotope is complexed to a binding agent attached to a fragment of an immunoglobulin such as Fab'. A clearing agent such as D-lysine may be administered to the patient along with the radioimmunoconjugate so that targeted tumor or cancer cells are destroyed, but damage to organs and tissues is minimized. After administering a radioimmunoconjugate to a patient, bone marrow or autologous stem-cells may be grafted to the patient.

2. Related Art

One therapeutic method used in cancer treatment involves directing antibodies carrying a therapeutic agent or cytotoxic compound to the diseased tissues. When localized at the disease site, the antibody delivers the therapeutic agent or cytotoxic compound to the cancerous cells. One approach to this methodology involves delivering radioisotopes to the diseased cells. This approach has proven useful in diagnosis where a radioisotope with particular imaging properties is delivered to the targeted diseased tissue.

Several methods have been used in radioimmunotherapy (RAIT). In one method, a radioisotope with desirable properties is carried by an antibody to a diseased tissue with a corresponding antigen. Various immunoglobulins such as IgG and IgM have been used to carry radioisotopes to an antigen located on a targeted disease tissue.

Various radioisotopes have been used in RAIT. $^{212}$Bi and its parent $^{212}$Pb have been successfully chelated to antibodies and other proteins via DTPA (diethylenetriamine pentaacetic acid) and DOTA (tetraazacyclododecane-N,N',N'',N'''-tetraacetic acid) derivatives and used as alpha emitting radioisotopes in RAIT. For example, Macklis et al. disclose a radioimmunoconjugate directed against a murine antigen present on the surface of malignant T-cells. Science, 240, 1024, 1988. The radioimmunoconjugate disclosed by Macklis et al. includes a $^{212}$Bi complexed to a cyclic anhydride of DTPA attached to a monoclonal antibody. Science, 240, 1024, 1988. One drawback to the use of $^{212}$Bi and its parent $^{212}$Pb in RAIT is that the decay product of $^{212}$Bi is $^{209}$Tl which is a high-energy β and γ-emitter. This characteristic raises radiation protection problems.

Another alpha-emitting radioisotope that has been investigated in immunotherapy is $^{211}$At. Bloomer et al. Science, 212, 340, 1988. The half-life of $^{211}$At of 7.2 hours is significantly longer than that of $^{212}$Bi which has a half-life of only 60.55 minutes. It is known that $^{211}$At undergoes 42% alpha decay and 58% electron capture. The alpha particle emitted upon decay has an energy of 5.94 MeV whereas electron capture produces 80 keV of γ radiation. The $^{211}$Po daughter arising from electron capture has a half-life of 0.5 seconds and decays by emitting an alpha particle with an energy of 7.43 MeV. Thus, by either rouite one obtains one high energy alpha particle per $^{211}$At decay. Isotopically pure $^{211}$At is accessible by electron capture of $^{211}$Rn which can be isolated in radiochemically pure form from irradiated thorium by gas chromatography. Chalkin et al. Chemiker-Ztg., 101, 470, 1977.

Astatine is a halogen atom and thus behaves similarly to iodine. It has long been known that blood clearance of $^{211}$At is very rapid because the astatine is quickly accumulated in the thyroid gland. Hamilton et al. *Proc. Nat'l. Acad. Sci.*, 26, 483, 1940. In fact, studies performed on rats and monkeys in the 1950's confirmed that the concentration of astatine in the thyroid is at least twvo orders of magnitude higher than in other organs, except for the stomach. Hamilton et al. *Univ. Calif. Pubi. Pharmacol.*, 2, 283, 1954.

Another radioisotope that has been investigated in conjunction with RAIT is $^{213}$Bi. This radioisotope is known to decay mainly (98%) by β and 440 keV γ emission with a half-life of 45.6 minutes to the ultra-short lived high-energy (8.375 MeV) alpha-emitter $^{213}$Po ($t_{1/2}$ of 4 μs), whereas a direct alpha-decay pathway to $^{209}$Tl plays only a negligible role (2% of all $^{213}$Bi decays).

U.S. Pat. No. 5,641,471 issued to Geerlings discloses a method for preparing $^{213}$Bi for therapeutic use. In the disclosed method a monoclonal antibody is used as a targeting moiety. A chelator such as CHX-DTPA (cyclohexyldiethylenetriamine pentaacetic acid) is attached to the antibody and functions to chelate the radioisotope. In this manner, the radioisotope is delivered to the target cell where it can function in a therapeutic manner to destroy the diseased tissue.

U.S. Pat. No. 5,246,691 issued to Geerlings et al. discloses radioimmunotherapy using alpha particle emissions. Specifically disclosed, is the use of $^{225}$Ac and its daughters as part of an immunoconjugate also comprising an antibody such as human monoclonal antibody and humanized antibodies. The cited patent discloses that chelating agents are used to bind actinium and bismuth radioisotopes in the radioimmunoconjugate comprising a radionuclide that emits alpha particles, a chelating agent, and a slowly localizing antibody such as a human IgM antibody. Also disclosed is the use of scavenging agents such as DTPA, EDTA, PLED, and crown ethers for use in binding wandering isotopes and thus prohibiting the isotopes from invading non-targeted organs and tissues.

U.S. Pat. No. 5,428,154 issued to Gansow et al. discloses a chelate comprising a DOTA derivative and a metal including Pb, Bi, Y, and the lanthanides. Also disclosed is the linking of the metal chelate to a biomolecule to form a delivery system for the chelated metal. Gansow et al. discloses that both alpha and beta-emitters ($^{212}$Pb, $^{212}$Bi, and $^{90}$Y) can be chelated to a DOTA derivative attached to a monoclonal antibody directed against an epitope on tumor cells.

A number of references have described radioimmunoconjugates comprising a radioisotope, and a chelator attached to a monoclonal antibody. Hovever, a need remains for a radioimmunoconjugate that utilizes a Fab' fragment of an immunoglobulin to target diseased tissue or cancer cells. A need also remains for a method of treating a patient that minimizes the amount of damage done by unbound radioisotopes.

OBJECTS OF THE INVENTION

It is an object of the present invention to provide a radloimmunoconjugate including a cytotoxic radioisotope bound to a binding site linked to or on an antigen-binding fragment of an antibody which specifically binds to a tumor-associated antigen.

Another object of the invention is to provide a method of treating a patient comprising administering to a patient a radioimmunoconjugate capable of targeting a diseased cell or tissue and delivering a radioisotope to the targeted cell or tissue.

Still another object of the invention is to provide a method of treating a patient that minimizes damage to non-targeted organs and tissues.

It is still another object of the invention to provide a method of treating a patient comprising administering a clearing agent to the patient in conjunction with a radioimmunoconjugate.

It is another object of the invention to provide a kit for use in radioimmunotherapy that includes a molecule with a radioisotope binding site linked to or on an antigen-binding fragment of an antibody which specifically binds to a tumor-associated antigen, and at least one clearing agent.

SUMMARY OF THE INVENTION

The present invention relates to radioimmunoconjugates including a cytotoxic radioisotope bound to a binding site linked to or on an antigen-binding fragment of an antibody which specifically binds to a tumor-associated antigen.

In preferred embodiments of the invention, the antibody is an IgG. In still other preferred embodiments of the invention, the fragment is a Fab' fragment. In especially preferred embodiments, the Fab' fragment is human, humanized or chimeric.

In preferred embodiments of the invention, the radioisotope of the radioimmunoconjugate is an alpha or beta emitter. More preferred embodiments include an alpha emitting radioisotope, and in the other preferred embodiments the radioisotope of the radioimmunoconjugate is $^{213}Bi$, $^{90}Y$, or $^{211}At$.

In other preferred embodiments of the invention, the binding site of the radioimmunoconjugate is selected from the group consisting of DTPA, DOTA, EDTA, PLED, a crown ether, an aromatic compound, and the sulfhydryl group of a cysteine residue on a Fab' fragment.

The present invention also relates to methods for treating a patient using the radioimmunoconjugate of the present invention.

In one embodiment, a method for treating a patient comprises administering any of the radioimmunoconjugates of the present invention to a patient. Other preferred embodiments comprise administering one or more clearing agents to a patient in conjunction with the administration of a radioimmunoconjugate. In more preferred embodiments, the clearing agent or agents are selected from the group consisting of an amino acid or peptide bearing an additional basic nitrogen functionality, a metal-chelating clearing agent, and an antibody or antibody fragment directed to an antigen on an antibody or antibody fragment which specifically binds to a tumor-associated antigen. In even more preferred embodiments, the clearing agent or agents are selected from the group consisting of lysine, polylysine, DOTA, DTPA, PLED, EDTA, and anti-idiotypic Fab' fragments. In especially preferred embodiments, the clearing agent is selected from the group consisting of lysine, polylysine, and galactosylated anti-idiotypic Fab' fragments. In still more preferred embodiments, the galactosylated anti-idiotypic Fab' fragments are humanized or chimeric Fab' fragments.

In other preferred embodiments, a method for treating a patient includes administering a radioimmunoconjugate of the present invention to a patient and subsequently grafting bone marrow or autologous stem cells to the patient.

In still other preferred embodiments, a method for treating a patient includes administering a radioimmunoconjugate of the present invention to a patient in conjunction with a clearing agent as described above and subsequently grafting bone marrow or autologous stem cells to the patient.

Other preferred embodiments of the invention provide a kit for use in radioimmunotherapy, comprising a molecule with a radioisotope binding site linked to or on an antigen-binding fragment of an antibody which specifically binds to a tumor-associated antigen, and at least one clearing agent.

More preferred embodiments of the invention provide a kit for use in radioimmunotherapy as described above wherein the clearing agent is selected from the group consisting of chelating clearing agents, an antibody or antibody fragment directed to an antigen on an antibody or antibody fragment which specifically binds to a tumor associated antigen, and clearing agents which prevent reuptake of small molecules and ions in the tubules of the kidney.

Other preferred embodiment of the invention provide a kit for use in radioimmunotherapy as described above wherein the at least one clearing agent is selected from the group consisting of DTPA, DOTA, EDTA, PLED, D-lysine, polylysine, and anti-idiotypic antibody Fab' fragments. In especially preferred embodiments, the kit provides at least one clearing agent, wherein the clearing agent is an anti-idiotypic galactosylated Fab' fragment, and in other even more preferred embodiments the anti-idiotypic galactosylated Fab' fragment is a chimeric or humanized Fab' fragment.

Additional aspects, features and advantages of the invention will be set forth in the description which follows, and in part will be obvious from the description, or may be learned by practice of the invention. The embodiments and advantages of the invention may be realized and obtained by means of the instrumentalities and combinations particularly pointed out in the appended claims.

DETAILED DESCRIPTION

Generally, the present invention provides a radioimmunoconjugate directed to a diseased tissue target. The radioimmunoconjugates of the present invention comprise a cytotoxic radioisotope bound to a binding site linked to or on an antigen-binding fragment of an antibody which specifically binds to a tumor-associated antigen.

Generally, the present invention also provides a method for treating a patient comprising administering a radioimmunoconjugate of the present invention to a patient. Preferably, the radioimmunoconjugate is administered to a patient in conjunction with one or more clearing agents to prevent unbound radioisotope from accumulating in and damaging organs and tissues in the body. Another preferred method of treating a patient comprises administering a radioimmunoconjugate to a patient and subsequently grafting bone marrow or autologous stem cells to the patient. A most preferred method of treatment comprises administering a radioimmunoconjugate of the present invention to a patient in conjunction with one or more clearing agents and subsequently grafting bone marrow or autologous stem cells to the patient.

The radioisotopes of the present invention include both alpha and beta emitting radioisotopes. Preferred radioisotopes of the present invention include alpha-emitting radioisotopes. Especially preferred radioisotopes of the present invention include $^{213}Bi$, $^{90}Y$, and $^{211}At$.

The radioimmunoconjugates of the present invention include a binding site linked to or on an antigen-binding fragment of an antibody which specifically binds to a tumor-associated antigen. Preferably, the antibody is an IgG immunoglobulin. However, it should be noted that the fragment of an antibody can be a fragment of any of the immunoglobulin types that binds to an antigen on the surface of diseased tissue or cancer cells. The antigen-binding fragment of the antibody which specifically binds to a tumor-associated antigen is preferably a Fab' fragment. Especially preferred are Fab' fragments which are humanized or chimeric in nature such that immunogenic response is minimized. Humanized and chimeric Fab' fragments may be prepared by methods known to those skilled in the art.

The binding site attached to a fragment of an antibody includes groups that chelate and those that are covalently bonded to a radioisotope of the present invention. The binding site of the present invention thus includes the sulfhydryl (SH) group on the cysteine residue on Fab' fragments after cleavage of the disulfide linkage. The sulfhydryl group will be found to bind many radiometal cations including various isotopes of lead and bismuth. The binding site also includes groups such as DTPA, DOTA, PLED, EDTA, crown ethers, cryptands, various phosphines including, but not limited to, diphosphines and triphosphines, thiols and any other chelating group that is known by those skilled in the art to bind the radioisotopes of the present invention. Preferred binding sites include DTPA and DOTA.

As described above, the term binding site as used herein is broad enough to encompass groups that are covalently attached to a radioisotope. This is particularly relevant to radioisotopes such as $^{211}$At which forms covalent bonds to various classes of organic compounds e.g. toluenes, phenols and phenol ethers (e.g. tyrosine, 4-methoxyphenylalanine, and anisole), benzene, anilines, imidazoles, phenylalanine, and pyrimidines among others. Thus, the term binding site attached to a fragment of an antibody in this context refers to the group to which the astatine isotope is covalently attached.

One or more clearing agents can be used to practice the method of the invention. Clearing agents in this context serve several different purposes. Non-targeted antibody fragment conjugate advantageously is cleared from circulation after sufficient time has elapsed for it to accrete at the target site. The clearing agent can be an antibody that specifically binds to any part of the conjugate. To the extent that the therapeutic radioisotope becomes detached from its binding site, usually a chelator, it advantageously is cleared with a chelating clearing agent. Glycosylation of clearing agents such as the foregoing can increase the rate of clearance by inducing rapid uptake by glycoside receptors in the liver. A further aid to clearance of non-targeted radioisotope can be achieved by the use of clearing agents that inhibit reuptake of small molecules in the kidney tubules. This mitigates radiation damage to the kidneys and accelerates clearance through the urinary bladder. It will be appreciated that combinations of these clearing agents advantageously are used to obtain the benefits each provides.

One type of clearing agent of the present invention includes metal-chelating agents that bind radioisotopes in the environment of the human body. Examples of this type of clearing agent include DTPA, DOTA, EDTA, PLED, and other materials known to those skilled in the art. Another type of clearing agent includes antibodies or antibody fragments directed against an epitope on an antibody or antibody fragment which specifically binds to a tumor-associated antigen. Preferred clearing agents of this class include anti-idiotypic clearing agents in which the clearing agent is an antibody or antibody fragment directed to the paratope of the antibody or antibody fragment directed to an antigen on a tumor or cancer cell.

Other preferred clearing agents include galactosylated antibodies or antibody fragments which exhibit enhanced clearing ability. Suitable such agents include but are not limited to galactose-second-Ab-Fab', where the second Ab binds to the targeting Ab. Other preferred clearing agents of this class include chimeric or humanized anti-idiotypic antibodies or antibody fragments, and particularly preferred clearing agents of this class are galactosylated humanized anti-idiotypic Fab' fragments such as galactose-W12-Fab'.

Another type of clearing agent of the present invention prevents reuptake of small molecules and ions in the tubules of the kidney. Such clearing agents include both amino acids and peptides bearing a basic nitrogen functionality in addition to the α-amino group found on naturally occurring amino acids. Thus, this class of clearing agents includes both enantiomers of lysine, ornithine, histidine, and arginine in addition to polymers such as polylysine. However, the D amino acids of lysine, ornithine, histidine, and argue are preferred clearing agents of this type, and D-lysine is especially preferred. Also preferred, are polymers of lysine such as polylysine.

Because the three types of clearing agent work in different ways, they may be used together to enhance removal of undesired species from the system. Preferably, a clearing agent of the type that prevents reuptake of small molecules and ions in the tubules of the kidney is used in conjunction with a clearing agent of the type which is an antibody or fragment of an antibody directed to an antigen on the surface of the targeting antibody or antibody fragment. Especially preferred is the use of a galactosylated anti-idiotypic fragment of an antibody which is directed to the paratope on the targeting antibody or antibody fragment in conjunction with either enantiomer of lysine. Also preferred, is the use of a chelating clearing agent to facilitate removal of free radioisotope with the above clearing agent combinations.

The present invention also provides a kit for use in RAIT. The kits of the present invention include the uncomplexed radioimmunoconjugate of the present invention which can also be described as a molecule with a radioisotope binding site linked to or on an antigen-binding antibody fragment which specifically binds to a tumor-associated antigen. The kits also include at least one clearing agent as described above. Preferable clearing agents for use in the kit include those which prevent reuptake of small molecules and ions in the kidney tubules such as lysine and polyl sine; those which chelate metals such as DOTA, DTPA, PLED, and EDTA; and those antibodies or antibody fragments, especially Fab' fragments, which are directed to the molecule with a radioisotope binding site.

The kits of the present invention are intended to be used in the treatment of patients having diseased target tissue bearing the antigen to which the molecule with a radioisotope binding site specifically binds. Thus, the molecule with the radioisotope binding site can be mixed with a radioisotope such as $^{213}$Bi or $^{90}$Y to prepare a radioimmunoconjugate of the present invention. The radioimmunoconjugate may then be injected into the patient followed by injection of the clearing agent to minimize damage to bone marrow, liver, kidneys, and other organs. A clearing agent that prevents the reuptake of small molecules in the kidney tubules may be injected prior to, with, or after injection of the radioimmunoconjugate. In this manner, the targeted tissue may be destroyed while minimizing damage to untargeted tissues or organs. Although the kits of the present invention include at least one clearing agent, the kits may contain other clearing agents. For example, a preferred kit of the present may include a chimeric or humanized galactosylated anti-idiotypic clearing agent and lysine to be used in conjunction for minimizing damage to non-targeted tissue or organs and additionally preventing reuptake in the kidney tubules.

The present invention may be embodied in other specific forms without departing from its spirit or its central characteristics. The described embodiments are to be considered in all respects only as illustrative and not restrictive. The scope of the invention is, therefore, indicated by the appended claims, rather than by the foregoing or following description. All changes which come within the meaning and range of equivalency of the claims are to be embraced within their scope.

Experiments were conducted to examine the efficacy of the radioimmunoconjugates of the present invention as therapeutic agents in the treatment of cancer and diseased tissue. These studies found that radioimmunoconjugates of both $^{213}$Bi and $^{90}$Y were highly effective in treating tumors induced by intrasplenic injection of human colon cancer cell line, GW-39, in mice.

A murine monoclonal antibody CO17-1A, an $IgG_{2a}$ isotype, was chosen as the immunoglobulin for the experiments. It is directed against a 41 kD glycoprotein found on human gastrointestinal malignancies. CO17-1A has an affinity constant of $5\times10^7$ l/mol to its antigen. After binding to the antigen, CO17-1A is readily internalized into the antigen-expressing tumor cells. The anti-human-CD3 antibody, OKT3, was used as irrelevant isotype-matched control. OKIT3 is ailso a murine $IgG_{2a}$ isotype and was obtained from CILAG (Sulzbach/Taunus, Germany).

Tumors were induced in female nude mice by injecting them with 200 μL of a 20 percent cell suspension of human carcinoma cell line, GW-39 serially propagated by preparing a mince through a 40 mesh screen and rinsings with Hank's balanced salt solution. After waiting approximately 10 days, tumors reached a size of 100-200 mg, and the mice were then used in the experiment.

Fab' fragments of CO17-1A were prepared from the complete immunoglobulin by pepsin digestion followed by subsequent disulfide reduction with cysteine. After purification and blocking with iodoacetamide, the Fab' fragments were reacted with isothiocyanate benzyl-DTPA to prepare the CO17-1A DTPA-Bz-Fab' conjugate. After purification, the DTPA-Bz-Fab' fragments were separately reacted with $^{213}$Bi, $^{90}$Y, and $^{88}$Y salts to produce the radioimmunoconjugates of the present invention, and the $^{88}$Y complex was used to analyze biodistribution. The prepared radioimmunoconjugates were injected into the mice within 20 minutes of their final preparation.

The biodistribution of bismuth versus yttrium-containing CO17-1A Fab' were compared to free $Bi^{3+}$ or $Y^{3+}$ in tumor, blood, kidneys and bone of subcutaneous GW-39 tumor-bearing nude mice. Due to the short physical half-life of $^{213}$Bi, biodistribittion studies were performed up to 5 hours post injection in contrast to one week with yttrium-containing conjugates. No significant differences were observed between the biokinetics of $^{213}$Bi- or $^{90}$Y-containing immuno-conjugates. The blood clearance was bi-exponential, with similar half-lives ($t_{1/2}$ ($\alpha$) ≈15 min, $t_{1/2}$ ($\beta$)≈5 hours) to those observed with radioiodinated Fab' fragments. The uptake in the tumor was rapid, reaching its apogee as early as 1-4 hours post injection (approximately 4% ID/g). Renal accretion was predominant, with maximum uptake values of up to ≧80% ID/g. Application of D-lysine reduced the renal accretion four to five fold.

In contrast, it was shown that free bismuth exhibits a very high renal accretion (up to 150% ID/g), which cannot be blocked by lysine, whereas yttrium ions are well known to be bone-seeking. The comparison clearly shows in vivo stability of the conjugates compared to the free ions.

Maximum tolerated dose finding trials of $^{213}$Bi- and $^{90}$Y-containing CO17-1A Fab' were undertaken. For this purpose, varying amounts of activity were injected starting at 100 μCi and increasing in 10 to 20 percent steps. At each activity level, one group of animals (10 to 20 per group) received the bismuth or yttrium with no additional support, and a second group was treated with D-lysine. Blood counts (white blood cells and platelets), blood urea nitrogen (BUN) and creatinine as well as alkaline phosphatase and glutamate oxaloacetate transaminase were determined on the day of radioimmunoconjugate administration and at weekly intervals thereafter. Acute treatment-related death was defined as occurring within four weeks post RAIT, whereas later deaths were regarded as chronic toxicity, if these deaths could not be related to tumor growth.

700 μCi of $^{213}$Bi-CO17-1A Fab', and 250 μCi of its $^{90}$Y counterpart were tolerated by all animals without acute treatment-related lethality, regardless of lysine administration. A 10% increase of these activities resulted in an at least 10% lethality. The blood cell counts and BUN levels at these respective maximum tolerated activities for $^{213}$Bi- and $^{90}$Y-Fab', respectively, were determined. The nadirs of leukocyte and thrombocyte counts were reached at 1 week after radio-antibody administration, and at both respective maximum tolerated activities, the severity of myelotoxicity was not significantly different, regardless of the radionuclide. The recovery from myelotoxicity, however, appeared faster with the shorter-lived $^{213}$Bi than with the $^{90}$Y. Thus, with $^{213}$Bi-Fab' the time to complete recovery was two to three weeks post therapy while with $^{90}$Y-Fab' the time to complete recovery was three to four weeks.

No significant differences with respect to the severity of acute myelotoxicity were observed whether the animals were given D-lysine or not. However, at a dose level of 300 μCi of $^{90}$Y-Fab', all animals without kidney protection died as compared to a 50% mortality when they were treated with D-lysine. In contrast, myelotoxicity-related lethality rates were similar at 800 (15% lethality) and 900 μCi (35% deaths) of $^{213}$Bi-Fab' regardless of whether or not lysine vas given.

In contrast, profound differences with respect to chronic toxicity were observed between animals given lysine and those not given lysine. The data show that in non-lysine treated animals, after a transient (2-3 weeks) episode of BUN elevation with subsequent normalization, BUN levels began to rise at six to seven weeks after therapy. The serum creatinine level followed the BUN value, but was less sensitive than the latter. The development of chronic renal failure was more dramatic (more steeply rising BUN levels in the $^{90}$Y than in the $^{213}$Bi-treated (groups. All animals treated with 250 μCi $^{90}$Y-Fab' without lysine protection died within three months after therapy, whereas the lethality of animals given 700 μCi of $^{213}$Bi-Fab' was only 15% after 5 months. Lysine treated groups survived without any signs of renal compromise, and there was no induction of renal insufficiency even six months after treatment. When combining kidney protection by lysine with bone marrow transplantation, the animals survived 400 μCi of $^{90}$Y- and 1100 μCi of $^{213}$Bi-CO17-1A-Fab', whereas 10% higher activities again led to an at least 10% lethality.

The therapeutic effect of $^{213}$Bi- versus $^{90}$Y-containing CO17-1A-Fab' at their respective maximum tolerated doses without or with bone marrow transplantation in subcutaneous GW-39 bearing animals also was studied. Both radioimmunoconjugates led to a significant growth retardation as compared to untreated controls or animals treated with the same activities of the Fab' fragment of the irrelevant antibody OKT3. Anti-tumor effects improved with dose-intensification. However, at each maximum tolerated dose $^{213}$Bi-Fab' was therapeutically superior to its $^{90}$Y-Fab' analog, whereas no significant differences were observed between both radioisotopes with the irrelevant OKT3 Fab'.

The survival of animals bearing GW-39 liver metastases was determined. Groups of twenty animals each were left untreated, were given 250 μCi of $^{90}$Y-CO17-1A or irrelevant OKT3-Fab', or 700 μCi $^{213}$Bi-CO17-1A or irrelevant OKT3-Fab' at two weeks after tumor inoculation. Each of these groups was placed under kidney protection with D-lysine. Untreated animals died within six to eight weeks of rapidly progressing liver metastases. The survival of animals treated with the irrelevant antibody was prolonged only for one to three weeks, regardless of the radioisotope. In contrast, the mean survival of animals treated with $^{90}$Y-Fab' was fifteen weeks, and twenty percent of mice treated in this manner survived for more than 30 weeks. Histology could not demonstrate any viable tumor cells in these long-term survivors. Thus, these animals were regarded as cured. The 95% cure rate of animals treated with $^{213}$Bi-CO17-1A-Fab' was significantly higher than that for animals treated with its $^{90}$Y analog.

An external scintigraphic scan of two mice bearing multiple GW-39 liver metastases at one hour after the injection of 700 μCi of $^{213}$Bi-CO17-1A-Fab' without or with D-lysine administration shows the effect of lysine administration on the renal accretion of $^{213}$Bi-CO17-1A-Fab', and it shows good tumor uptake in multiple metastatic lesions in the liver.

The radiation dosimetry of $^{213}$Bi- versus $^{90}$Y-containing CO17-1A-Fab' in subcutaneous GW-39 xerograft bearing nude mice, based on the biodistribution studies is summarized in Table 1. The model of Yoriyaz and Stabin was used since high energy β-emitters like $^{90}$Y result in cross-organ irradiation. For the dosimetry of $^{90}$Y-CO17-1A-Fab', the table accounts for crossrgan radiation, and for $^{213}$Bi-CO17-1A-Fab', it differentiates into doses resulting merely from the self-absorption of the α particles of $^{213}$Po (first column) or including the β and γ rays of $^{213}$Bi (with potential inter-organ crossfire, second column).

TABLE 1

Radiation dosimetry of $^{213}$Bi- versus $^{90}$Y-containing CO17-1A-Fab' in subcutaneous GW-39 xerograft bearing nude mice. MTD stands for maximum tolerated dose.

| Organ/Tissue | $^{90}$Y-CO17-1A-Fab' Dose (Gy/mCi) β with cross | $^{90}$Y-CO17-1A-Fab' Dose at the MTD Convent. (Gy/250 μCi) | $^{90}$Y-CO17-1A-Fab' Dose at the MTD Lysine + BMT (Gy/400 μCi) | $^{213}$Bi-CO17-1A-Fab' Dose (Gy/mCi) α self | $^{213}$Bi-CO17-1A-Fab' Dose (Gy/mCi) α + β/γ w/cross | $^{213}$Bi-CO17-1A-Fab' Dose at the MTD Convent. (Gy/700 μCi) | $^{213}$Bi-CO17-1A-Fab' Dose at the MTD Lysine + BMT (Gy/1100 μCi) |
|---|---|---|---|---|---|---|---|
| Tumor | 54.0 | 13.5 | 21.6 | 12.8 | 13.0 | 9.1 | 14.3 |
| Liver | 45.4 | 11.3 | — | 5.6 | 5.9 | 4.1 | — |
| Liver + lysine | 40.4 | 10.1 | 16.2 | 5.6 | 5.8 | 4.1 | 6.4 |
| Spleen | 36.7 | 9.2 | — | 5.7 | 6.0 | 4.2 | — |
| Spleen + lysine | 25.1 | 6.3 | 10.0 | 5.7 | 5.9 | 4.1 | 6.5 |
| Kidney | 279.2 | 69.8 | — | 74.2 | 77.3 | 54.1 | — |
| Kidney + lysine | 73.2 | 18.3 | 29.0 | 29.3 | 29.5 | 20.7 | 32.5 |
| Lung | 11.6 | 2.9 | 4.6 | 6.7 | 6.9 | 4.8 | 7.6 |
| Intestine | 37.7 | 9.4 | — | 2.6 | 2.9 | 2.0 | — |
| Intestine + lysine | 31.2 | 7.8 | 12.5 | 2.6 | 2.8 | 2.0 | 3.1 |
| Bone | 27.0 | 6.8 | 10.8 | 3.5 | 3.7 | 2.6 | 4.1 |
| Blood | 23.4 | 5.4 | 9.4 | 10.5 | 10.9 | 7.6 | 12.0 |

As a result of tumor growth-retardation being the major observed effect in all treated groups, the correlation between mean tumor doses and the extent of induced growth retardation was an important measure of the activities of the radioimmunoconugates. Since GW-39 is a very rapidly-growing cell line with tumor-volume doubling times of less than one week, the correlation between tumor doses and the mean time needed for quadruplication of tumor volume was analyzed. With $^{90}$-Fab', below a tumor dose of approximately 5 Gy, no significant tumor growth delay was noticeable. Above the threshold, tumor growth was retarded in a dose-dependent fashion up to seven-fold at approximately 20 Gy. The resulting non-linear regression curve (regression coefficient: r=0.96) resembles a shoulder curve with its shoulder at approximately 5 Gy. In distinct contrast, no threshold dose was seen with the $^{213}$Bi-CO17-1A-Fab', and the time to tumor volume quadruplication was prolonged in an almost linearly increasing manner with increasing tumor dose (regression coefficient: r=0.98). Comparable anti-tumor efficacy was seen with $^{213}$Bi-CO17-1A-Fab' at doses which were approximately half as high as those needed with the $^{90}$Y radioisotope.

EXAMPLES

Example 1

Preparation of a Fab' Fragment of an IgG Immunoglobulin

A Fab' fragment of an IgG immunoglobulin (murine monoclonal antibody CO171A, obtained from GlaxoWellcome (Hamburg, Germany)) was prepared from complete IgG by pepsin digestion (Immunopure® F(ab')$_2$ preparation kit, Pierce, Rockford, ill.) followed by reduction with a low molecular weight thiol. Generally, the IgG immunoglobulin was incubated with 200 µg/µL of pepsin at a pH of 4 for one hour. The resulting mixture was purified by a tandem column of protein A, to remove the undigested IgG, followed by a G-50 Sephadex, to remove low molecular weight contaminants. Subsequent disulfide reduction in 0.1 M phosphate buffered saline containing 10 mM EDTA in the presence of 10 mM cysteine for 12 hours at 37° C. yielded the Fab'-SH fragment. The progress of (lie reduction reaction was followed by HPLC, and when complete the Fab'-SH as purified as described below.

Example 2

Purification of Fab'-SH Fragment

Fab'-SH fragments prepared as described in Example 1 were purified by protein A chromatography and exhaustive ultrafiltrations. The purified Fab'-SH fragments were stored in deoxygenated buffer at a pH of less than 5 containing 10 mM EDTA.

Example 3

Preparation of Iodoacetamide-Blocked Fab' Fragments

The Fab'-SH fragments purified according to Example 2 were reacted with excess iodoacetamide to block the hinge-region thiol groups and prevent reassociation of the fragments. The iodoacetamide-blocked Fab' fragments were repurified from excess iodoacetamide.

Example 4

Preparation of Thiol-Bound $^{213}$Bi Fab' Fragments

Incubation of the Fab'-SH fragments purified according to Example 2 with $^{213}$BiCl$_3$ results in reaction with the sulfhydryl groups (SH) groups on the cysteine residues of the Fab' fragments.

Example 5

Preparation of SCN-Bz-DTPA Conjugates of Iodoacetamide-Blocked Fab' Fragments

Isothiocyanate benzyl-diethylene-triamine-pentaacetate (SCN-Bz-DTPA) conjugates of iodoacetamide blocked Fab' fragments were prepared by stardard procedures. Briefly, SCN-Bz-DTPA was added to the Fab' fragments (5.0 mg/ml), previously dialyzed against 100 mM Hepes buffer, pH 8.6 containing 150 mM NaCl, at an 8:1 molar excess of DTPA to Mab. After overnight incubation at room temperature, the antibody conjugates were purified from unreacted SCN-Bz-DTPA by gel filtration chromatography on a 1×50 cm column of Sephadex G-50 (Sigma Chemie, Deisenhofen, Germany).

Example 6

Preparation of $^{213}$Bi-Containing SCN-Bz-DTPA Conjugates of Fab' Fragments $^{213}$Bi was obtained as a mixed iodide/chloride salt from an "in house" $^{225}$Ac/$^{213}$Bi generator as has been described in the literature. Briefly, $^{225}$Ac was purified after being obtained from a $^{229}$Th source (the latter being a decay product of $^{233}$U). $^{225}$Ac was dissolved in 2 M HCl and loaded onto a lead-shielded 4×40 mm column of AG MP-50 cation exchange resin (Bio-Rad Laboratories. Munich, Germany). $^{225}$Ac decays by α-/γ-decay with a 10.0 day half-life via two short-lived α-/γ-emitting intermediates ($^{221}$Fr and $^{217}$At) to $^{213}$Bi which was eluted in two-hourly intervals with 1 ml of 0.1 M NaI/0.1 M HCl. After each elution, the cation exchange column was washed with 5 bed volumes of 0.01 M HCl. The 0.1 M NaI/0.1 M HCl eluate containing the activity was buffered with 200 µl of 0.5 M NaOAc at pH 5.5, and the pH was adjusted with 50-70 µl of 1.0 At NaOH to a value of 5.5.

The $^{213}$Bi solution described above was added to a solution of the SCN-Bz-DTPA conjugate of Fab' buffered in 0.5 M NaOAc at a pH of 5.5 until a specific activity of 2-3 mCi/mg was achieved. The reaction mixture was incubated for 5 minutes at 37° C. The resulting $^{213}$Bi complex was purified from unbound $^{213}$Bi within 5 minutes using size exclusion chromatography on a PD-10 column (Sephadex G-25 pre-packed in a 15×50 mm column; Pharmacia, Uppsala, Sweden). Excess DTPA was added to complex any unbound bismuth. The quality of the complex was tested by HPLC (Bio-Sil SEC-250 column, 300×7.8 mm; Bio-Rad Laboratories, Richmond, Calif.) as well as by measuring its immunoreactivity. The amount of unbound isotope was less than 2 percent. Labeled antibody fragments were administered within 20 minutes of their final preparation.

Example 7

Preparation of Y-Containing SCN-Bz-DTPA Conjugates of Fab' Fragments

For biodistribution studies, $^{88}$Y was obtained as $^{88}$YCl$_3$ in 0.1 M HCl from Amersham Life Science (Braunschweig, Germany). For therapy studies, $^{90}$Y was obtained from Pacific Northwest National Laboratory (Richland, Wash.) as $^{90}$YCl$_3$ in 0.05 M HCl. The yttrium solution was added to a solution of the SCN-Bz-DTPA conjugate of Fab' buffered in 0.5 M NaOAc at a pH of 5.5 until a specific activity of 2-3 mCi/mg was achieved for $^{90}$Y. An equivalent amount was added to prepare the $^{88}$Y complexes. The reaction mixture was incubated for 5 minutes at 37° C. The resulting yttrium complexes were purified from unbound yttrium within 5 minutes using size exclusion chromatography on a PD-10 column (Sephadex G-25 pre-packed in a 15×50 mm column; Pharmacia, Uppsala, Sweden). Excess DTPA was added to complex any unbound yttrium. The quality of the complex was tested by HPLC (Bio-Sil SEC-250 column, 300×7.8 mm; Bio-Rad Laboratories, Richmond, Calif.) as well as by measuring its immunoreactivity. The amount of unbound isotope was less than 2 percent. Labeled antibody fragments were administered within 20 minutes of their final preparation.

Example 8

Preparation of Galactose-W12-Fab' Clearing Agent

The anti-idiotypic Ab to MN-14, termed W12 is digested to a F(ab')$_2$ fragment using pepsin, as outlined in Example 1. The F(ab')$_2$ is reduced to a Fab' fragment using a low molecular weight thiol as described in Example 1. At the end of the reduction, the Fab'-SH is purified by spin-column chromatography and reacted with excess iodoacetamide to block the hinge-region thiol groups and prevent reassociation of the fragments. After repurification with excess iodoacetamide, the Fab' is reacted with a 400-fold molar excess of the galactosylation agent, the thioimidate of cyanomethyl-2,3,4,6-tetra-O-acetyl-1-thio-beta-D galactopyranoside. The galactosylated protein is purified by two spin-columns and the galactose:Fab' ratio is determined by MALDI-MS.

Example 9

Induction of Carcinoma in Mice

Female nude mice, 19 to 23 g and 4 to 5 weeks old, were purchased from Charles River (Sulzfeld, Germany). The human colon carcinoma cell line, GW-39, was serially propagated by preparing a mince through a 40-mesh screen, and rinsing with sterile Hank's balanced salt solution (ICN Biomedicals, Eschiwege, Germany) to yield a 20 percent cell suspension. This suspension (200 µl) was injected subcutaneously into each of the mice. After approximately 10 days, tumors reached the size of approximately 100-200 mg. This was the size used for the purposes of the study.

Example 10

Biodistribution Study

Tumor-bearing mice as described in Example 9 were injected in the tail vein with the Fab' fragments containing the bismuth or yttrium radioisotopes at a protein amount of approximately 200-300 µg. The mice were sacrificed at 10 minutes, and at 1, 4, 24, 72, and 168 hours for $^{88}$Y, and at 10 minutes, and 1, 3 and 5 hours for the $^{213}$Bi Fab' complexes. The mice were bled by retroorbital puncture. For determining the whole-body retention, the mice were measured in a well counter. After cervical dislocation, the animals were dissected. The amount of activity in the tumors and tissues (liver, spleen, kidney, lung, heart, intestine, bone, and blood) was determined by gamma scintillation counting using an injection standard to account for physical decay. The number of animals used for each study was typically five animals per group at each time-point, and the tumor sizes were in the same range as those used for the actual therapy experiments.

Example 11

Radiation Dosimetry

The biodistribution data were used to generate time activity curves. Time-activity curves were fit to the difference or sum of two exponents for curves with and without an uptake component, respectively. Cumulated activity in each organ was obtained by analytically integrating the resulting expressions over time. Tumor and organ doses were calculated, accounting for the electrons of $^{90}$Y or the alpha particle, electron, and photon contributions of $^{213}$Bi and its daughter $^{213}$Po, but neglecting the $^{209}$Pb or $^{209}$Tl beta contributions. These dose calculations were performed according to the geometric model of a 30 g mouse by Yoriyaz and Stabin. This model accounts for cross-organ irradiation and the whole-body contribution by using the Monte Carlo transport simulation code MCNP4A. For obtaining bone marrow dose estimates, absorbed β fractions $\phi_\beta$ ($r_t \leftarrow r_s$) between bone and bone marrow were used.

Example 12

Experimental Radioimmunotherapy

Tumor sizes of subcutaneous tumors were determined by caliper measurement in three dimensions immediately before therapy and at weekly intervals thereafter. Animals were either left untreated (controls) or injected with a single dose of $^{90}$Y- or $^{213}$Bi-containing complexes with the activities indicated. Ten to twenty animals were studied in each treatment group. As a nonspecific therapy control, the Bz-DTPA-conjugated Fab' fragment of the anti-CD3 T-cell lymphoma monoclonal antibody OKT3 was used. Body weight was recorded weekly, and survival was monitored. The maximum tolerated dose (MTD) was defined as the highest possible dose under the respective conditions that did not result in any animal deaths, with the next higher dose level resulting in at least 10 percent of the animals dying. Animals were observed until their death or a loss of more than 30 percent of their original weight or until the tumor began to ulcerate through the skin, at which time they were removed from the group and sacrificed.

Example 13

Renal Uptake Reduction and Bone Marrow Transplantation

D-lysine monohydrochloride (Sigma Chemie, Deisenhofen, Germany) was dissolved in phosphate buffered saline at 175 mg/ml. The animals were injected intraparenterally with 200 µl of this solution (i.e., 35 mg of D-lysine) with four hourly injections, starting 30 minutes before administration of the radioimmunoconjugate.

Bone marrow was harvested by sterile technique from untreated donor nude mice of the same strain. The marrow cavity of both mouse femurs was rinsed with 0.9% sterile saline using 26 gauge needles. An inoculum of $10^7$ bone marrow cells was injected intravenously via the tail vein at 24 hours after radioimmunoconjugate injection.

Example 14

Determination of Blood Counts, Renal and Liver Function Parameters

Total and differential leuko- and thrombocyte counts were determined on the day of therapy, and at weekly intervals thereafter. 75 µl heparinized specimens were collected by retroorbital bleeding. The samples were counted on a Technicon H3 Auto-Analyzer (Bayer-Diagnostik, Munich, Germany). The means +/−standard deviation was calculated for each group. Blood urea nitrogen, creatinine, alkaline phosphatase, and glutamate oxaloacetate transaminase were determined on the day of radioimmunoconjugate injection and at weekly intervals thereafter. Each of these parameters were assayed according to assay procedures known to those skilled in the art.

Example 15

Histology

For organ and tumor histology, the animals were sacrificed by cervical dislocation and necropsied at the times indicated. Organs were fixed in 10% formalin, embedded in paraffin and cut into 5 µm sections. Staining was performed with hematoxylin-eosin.

Example 16

Statistical Analysis

Differences in the tissue uptake values and the biodistribution data were statistically analyzed with the Student's t-test for unpaired data. Pairwise comparisons were performed with the Wilcoxon Rank-Sum test. Differences in the therapeutic efficacy between the treatment modalities in subcutaneous tumors were analyzed by assuming an exponential tumor growth pattern; non-linear regression analysis based on asymptotic approximation was used. Survival analysis was based on the Kaplan-Meier product limit, and groups were compared using the log rank test. The log-rank test was also used for comparing times to tumor volume multiplication.

Example 17

Treatment of a Human Patient with a Radioisotope-Containing SCN-Bz-DTPA Conjugate of Fab' and a Clearing Agent A patient with a colorectal tumor is injected with D-Lysine prior to administration of a radioimmunoconjugate. Generally, the clearing agent or agents of the type that prevent reuptake in the tubules of the kidney is administered 24 hours to 30 minutes prior to injection of the radioimmunoconjugate. A radioisotope-containing the SCN-Bz-DTPA conjugate of Fab' prepared from MN-14 anti-CEA is then injected into the patient, and the patient is monitored during treatment. The radioisotope may be any alpha or beta emitting radioisotope that complexes to the conjugate such as, but not limited to $^{213}$Bi or $^{99}$Y. Additional D-lysine is generally administered to the patient after the radioimmunoconjugate has been injected. One or more clearing agents can be used separately or in combination. For example, D-lysine can be used in conjunction with DTPA-galactose-W12-Fab'. Clearing agents that specifically bind any part of the conjugate should not be administered until a sufficient time has elapsed for the radioimmunoconjugate to accrete at the target site. Thus, a galactosylated anti-idiotypic clearing agent such as DTPA-galactose-W12-Fab' is injected into the patient after a sufficient amount of the injected radioimmunoconjugate has localized to the tumor. Radiommunoconjugate localized at the tumor releases alpha or beta particles resulting in the destruction of tumor cells in the patient.

Example 18

Preparation of (BOC)Gly-D-Tyr(O-t-But)-D-Lys-OH

The synthesis of (BOC)Gly-D-Tyr(O-t-But)-D-Lys-OH uses amino acids protected with well-known protecting groups such as allyloxycarbonyl (Aloc) and 9-fluorenyl-methoxycarbonyl (Fmoc). First, Fmoc-D-Lys(Aloc) [0.325 g; 0.72 mmol] is dissolved in 5 ml of anhydrous dichloromethane ($CH_2Cl_2$), and mixed with 0.55 ml of diisopropylethylamine (DIEA). The solution is then added to 0.5 g of 2-chlorotrityl chloride resin in a 20 ml vial and the contents shaken vigorously for 18 hours. The reddish slurry is placed in a column assembly fitted with a frit and a 3-way stopcock which can be used to either bubble nitrogen through the slurry for mixing purposes or for draining solution off the column and leaving the resin on the column. The solution is drained off, and the resin is washed with 3×40 ml of $CH_2Cl_2$:MeOH:DIEA (17:2:1), 3×40 ml of $CH_2Cl_2$, 2×40 ml of DMF, 2×40 ml of $CH_2Cl_2$ and 2×40 ml of MeOH. The resin is dried under a flow of nitrogen. The Fmoc group is cleaved by adding 40 ml of 5% piperidine in 1:1 (v/v) $CH_2Cl_2$-DMF for 10 minutes, draining the solution off, and continuing cleavage with 20% piperidine in $CH_2Cl_2$-DMF for 15 minutes. This is followed by a wash cycle with 40 ml DMF, 40 ml isopropanol (IPA), 40 ml NMP (N-methylpyrrolidone), 40 ml IPA, and 4×40 ml NMP. The resin is then reacted with 1.8 mmol of activated Fmoc-D-Tyr(O-t-But) for 40 minutes. The activation is carried out using 0.827 g (1.8 mmol) of Fmoc-D-Tyr(O-t-But), 0.269 g of HOBT in 4 ml of NMP, adding to the clear solution 0.31 ml of diisopropylcarbodiimide (DIC), and maintaining at ambient temperature for 20 minutes. After this period, 3.6 mmol (0.62 ml) of DIEA is added, and the reaction is continued for 25 minutes. The wash sequence, following Fmoc cleavage and subsequent wash sequence, are as described above. A second coupling using activated BOC-Gly (derived from 0.376 g or 3 mmol of Boc-Gly) is carried out in an analogous manner. The Aloc group is removed using a solution of 0.1547 g of tetrakis (triphenylphosphine) palladium(0) in a mixture of $CH_2Cl_2$ (40 ml): AcOH (2 ml) and DIEA (5 ml), followed by the addition of 5 ml of tributyltin hydride. After the usual wash sequence, the peptide is cleaved from the resin with 10 ml of acetic acid-trifluoroethanol-$CH_2Cl_2$ (1:1:8 v/v). The cleaved peptide solution is concentrated to 0.25 g of the title compound (gummy product). The product exhibits a single peak with a retention time of 7.10 minutes on analytical reverse phase HPLC. Electrospray mass spectrum analysis showed an M+H peak at m/e 523 (positive ion mode) and an M-H peak at m/e 521 (negative ion mode).

Example 19

Preparation of Glv-D-Tyr-D-Lys(SCN-Bz-DTPA)-OH 0.053 g (0.1 mmol) of the product from Example 18 is mixed with SCN-Bz-DTPA (81 mg of 80% DTPA content; 20% excess) in water-dioxane, and the pH is adjusted to 8.5. The solution is incubated for 2.5 hours at 37° C. More SCN-Bz-DTPA (41 mg) is added, and the pH is readjusted to 8.56. The solution is then incubated for 2 hours at the same temperature. Preparative HPLC purification on reverse phase column using a gradient elution of water (0.1% TFA)/90% acetonitrile-water (0.1% TFA) furnishes 30 mg of (BOC)Gly-D-Tyr(O-t-But)-D-Lys(SCN-Bz-DTPA)-OH as a colorless solid. Analytical reverse phase HPLC shows a single peak with a retention time of 7.54 minutes. Mass spectrum analysis revealed an M+H peak at m/e 1063 (positive ion mode) and the M-H peak at m/e 1061 (negative ion mode). This material is then treated with a mixture of TFA/$CH_2Cl_2$/anisole for 1 hour, and the BOC- and Tyr(O-t-But) protecting groups are cleaved off. The title compound is precipitated by adding the reaction mixture to ethyl ether. The HPLC retention time was 5.31 minutes. Mass spectrum analysis showed an M+H peak at 907, and an M-H peak at 906.

Example 20

Preparation of (MCC)Gly-D-Tyr-D-Lys(SCN-Bz-DTPA)-OH 0.025 g (0.0138 mmol) of the product from Example 19 is dissolved in 0.5 ml of 0.1 M sodium phosphate solution at pH 7.0. To this solution, 0.03 g of commercially available sulfosuccinimidyl 4-(N-maleimidoniethyl)-1-carboxylate (SMCC) is added and the pH is raised to 7.17, and the clear solution is stirred for 1 hour. Preparative HPLC on a preparative reverse phase column using the same gradient elution as in Example 18 yields 0.0054 g of the title compound [where MCC stands for the 4-N-maleimidomethyl)-1-carbonyl moiety]. The retention time of the purified material (analytical RP column) is 6.36 minutes. Electrospray mass spectrum analysis showed an M+H peak at m/e 1126 and an M-H peak at m/e 1124.

Example 21

Astatination of Product from Example 20 and Attachment to Fab'-SH

The product of Example 20 is astatinated with ($^{211}$At)-sodium astatatide using chloramine T as oxidant for 1-2 minutes. The labeled substrate is transferred to a second vial, and treated with 4-hydroxyphenylacetic acid to remove unreacted astatide. The labeled substrate is reacted with the Fab'-SH fragment of Example 2 for 1-2 hours, and the solution is then made 5 mM in sodium tetrathionate, incubated for five minutes, and purified on a centrifuged size-exclusion column of Sephadex™ 50/80 in 0.1 M sodium phosphate pH 7. The purified $^{211}$At-containing radioimmunoconjugate is then administered to a patient.

The invention claimed is:

1. A method of treatment of a cancer comprising administering to a patient in need thereof: a molecule with a radioisotope binding site linked to or on an antigen-binding fragment of an antibody that specifically binds to a tumor-associated antigen; and at least two clearing agents, wherein said clearing agents are at least
    (A) a metal-chelating clearing agent, and
    (B) an amino acid bearing an amino basic side group or a peptide bearing an amino basic side group.

2. The method according to claim 1, wherein the amino acid or peptide clearing agent is selected from the group consisting of lysine, omithine, histidine, arginine, polylysine, and combinations thereof.

3. The method according to claim 1, wherein the amino acid is a D amino acid.

4. The method according to claim 1, wherein the amino acid is an L amino acid.

5. The method according to claim 1, further comprising administering an antibody directed to an epitope on the molecule, wherein the antibody acts as a clearing agent.

6. The method according to claim 5, wherein the antibody is a galactosylated antibody or antibody fragment that specifically binds the molecule.

7. The method according to claim 6, wherein the antibody is an anti-idiotypic clearing agent.

8. A method of treatment of a cancer comprising administering to a patient in need thereof: a molecule with a radioisotope binding site linked to or on an antigen-binding fragment of an antibody that specifically binds to a tumor-associated antigen; and at least two clearing agents, wherein said clearing agents are at least (A) an antibody directed to an epitope on the molecule, wherein the antibody acts as a clearing agent, and (B) an amino acid bearing an amino basic side group or a peptide bearing an amino basic side group.

9. The method according to claim 8, wherein amino acid or peptide clearing agent is selected from the group consisting of lysine, omithine, histidine, arginine, polylysine, and combinations thereof.

10. The method according to claim 8, wherein the antibody is a galactosylated antibody or antibody fragment that specifically binds the molecule.

11. The method according to claim 10, wherein the antibody is an anti-idiotypic clearing agent.

12. The method according to claim 8, wherein the amino acid is a D amino acid.

13. The method according to claim 8, wherein the amino acid is an L amino acid.

14. The method according to claim 8, further comprising administering a metal-chelating clearing agent.

* * * * *

UNITED STATES PATENT AND TRADEMARK OFFICE
CERTIFICATE OF CORRECTION

| | | |
|---|---|---|
| PATENT NO. | : 7,220,399 B2 | Page 1 of 1 |
| APPLICATION NO. | : 10/724397 | |
| DATED | : May 22, 2007 | |
| INVENTOR(S) | : David M. Goldenberg et al. | |

It is certified that error appears in the above-identified patent and that said Letters Patent is hereby corrected as shown below:

(Col. 17, line 21), please replace "omithine," with --ornithine--.

(Col. 18, line 16), please replace "omithine," with --ornithine--.

Signed and Sealed this

Fourth Day of September, 2007

JON W. DUDAS
*Director of the United States Patent and Trademark Office*